US009119857B2

(12) United States Patent
Azim et al.

(10) Patent No.: US 9,119,857 B2
(45) Date of Patent: Sep. 1, 2015

(54) SMALL MOLECULE ACTIVATORS OF HSIV PROTEASE FOR DEVELOPMENT OF NOVEL ANTIMICROBIALS

(71) Applicants: M. Kamran Azim, Karachi (PK); Yasmeen Rashid, Karachi (PK); Khalid M. Khan, Karachi (PK)

(72) Inventors: M. Kamran Azim, Karachi (PK); Yasmeen Rashid, Karachi (PK); Khalid M. Khan, Karachi (PK)

( * ) Notice: Subject to any disclaimer, the term of this patent is extended or adjusted under 35 U.S.C. 154(b) by 0 days.

(21) Appl. No.: 13/919,665

(22) Filed: Jun. 17, 2013

(65) Prior Publication Data

US 2014/0371248 A1 Dec. 18, 2014

(51) Int. Cl.

| | |
|---|---|
| *A01N 43/90* | (2006.01) |
| *A61K 31/517* | (2006.01) |
| *A61K 31/352* | (2006.01) |

(52) U.S. Cl.

CPC ............. *A61K 31/517* (2013.01); *A61K 31/352* (2013.01)

(58) Field of Classification Search

USPC .................................................... 514/266.31

See application file for complete search history.

(56) References Cited

PUBLICATIONS

Rashid et. al. (Bioorganic and Medicianal Chemistry letters (2012) 6089-6094).*

* cited by examiner

*Primary Examiner* — Marcos Sznaidman
(74) *Attorney, Agent, or Firm* — Sarfaraz Niazi

(57) ABSTRACT

HslVU is the proteasome-related system composed of HslV peptidase and HslU chaperone. It is involved in intracellular proteolysis. The presence of HslVU homologs in pathogenic microbes and its absence in human makes it an antimicrobial drug target. The functional HslVU complex forms when HslV dodecamer is flanked at both ends by HslU hexamers. In the HslVU complex, intercalation of C-termini residues of HslU subunits into the clefts between adjacent HslV subunits results in allosteric activation of HslV. We identified small molecules capable of activating HslV peptidase in the absence of its natural activator HslU. Quinazoline and chromone derivatives were suggested by ligand docking to bind at the HslU C-termini intercalation pockets in the HslV. This was confirmed by HslV activation assays with these compounds that gave $ED_{50}$ in sub-micromolar range. The results showed that small, extracellular non-peptidic molecules can activate the HslV peptidase which in turn would initiate intracellular proteolysis.

1 Claim, 6 Drawing Sheets

FIG. 1

```
               S1        S2      S2A  S2B       S3         S4                H1
E. coli        TTIVSVRRNGHVVIAGDGQATLGNTVMKGNVKKVRRLYNDKVIAGFAGGTADAFTLFELF
H. influenzae  TTIVSVRRNGQVVVGGDGQVSLGNTVMKGNARKVRRLYNGKVLAGFAGGTADAFTLFELF
               ***: *****:.*:.****.::*.**:***.:***:*  :.**:*****..***.***: *

H2         H2A    S5        S6       s7
E. coli        ERKLEMHQGHLVKAAVELAKDWRTDRMLRKLEALLAVADETASLIITGNGDVVQPEND-L
H. influenzae  ERKLEMHQGHLLKSAVELAKDWRTDRALRKLEAMLIVADEKESLIITGIGDVVQPEEDQI
               * **.     *:* *:********** :***:* *:   ::* *:*:**::* s8        H3              H4                s9
E. coli        IAIGSGGPYAQAAARALLENTELSAREIAEKALDIAGDICIYTNHFHTIEELSYK
H. influenzae  LAIGSGGNYALSAARALVENTELSAHEIVEKSLRIAGDICVFTNTNFTIEELP--
               ****** ** :**:**:.**:***:**.**::  ***:**::**   .***:
```

SMALL MOLECULE ACTIVATORS OF HSlV PROTEASE FOR DEVELOPMENT OF NOVEL ANTIMICROBIALS

Figure 1:
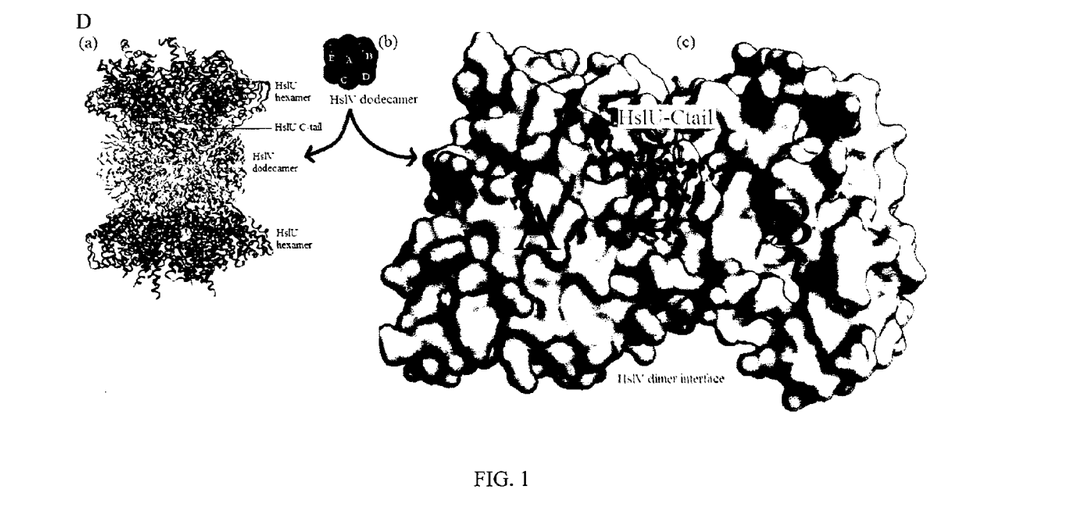
Figure 2:
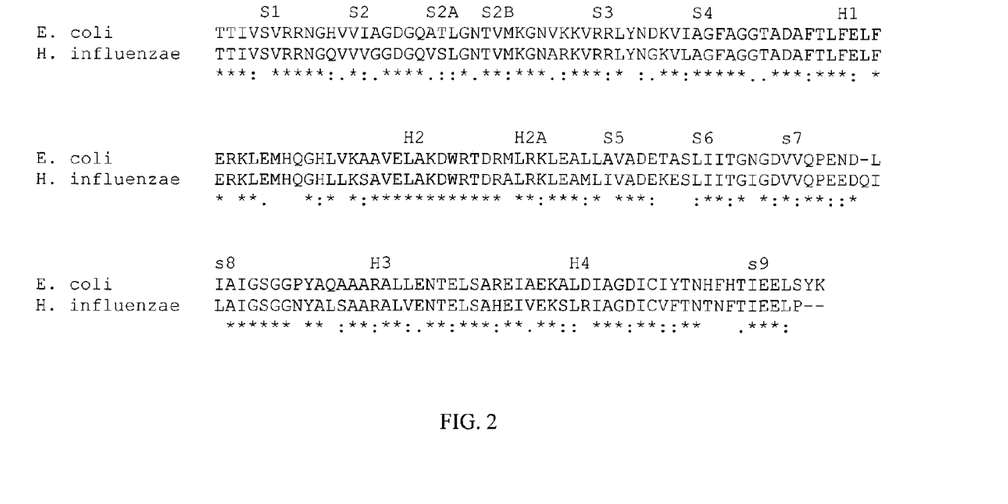

The text file named Sequence Listing 13919665 is hereby incorporated by reference.

BACKGROUND OF THE INVENTION

The HslVU protease-chaperone complex is a two component, proteasome-related system typical of eubacteria and well-known in eukaryotes. It is involved in intracellular degradation of a number of important proteins including transcription factors, cell cycle regulatory proteins and short-lived proteins. The HslVU is composed of multiple copies of two heat shock proteins, the 19 kDa HslV peptidase and the 50 kDa HslU, the ATPase and chaperone. The HslV is an N-terminal threonine protease related to the β-subunits of the 20S proteasome from eukaryotes and the archaebacteria. The HslV forms a barrel-shaped dodecameric complex by stacking two hexameric rings of HslV subunits and each of the HslV subunit contains an N-terminal Thr active site for proteolysis (FIG. 1). In the HslV dodecamer, the intra-ring interfaces are mainly stabilized by polar interactions whereas conserved hydrophobic residues are engaged to form the inter-ring interface. As a member of AAA-ATPase superfamily, the HslU demonstrates ATPase and unfoldase/chaperone activities simultaneously and related to the base part of the proteasomal 19S complex.

In the HslVU complex, the central pores of HslU and HslV are aligned, so that HslU transfers substrate poypeptides through the pores into inner proteolytic chamber of HslV. The HslV alone shows a very weak peptidase activity towards carbobenzoxy-Gly-Gly-Leu-7-amido-4-methyl coumarin (Z-GGL-AMC), a small fluorogenic peptide substrate, but its activity increases 1-2 orders of magnitude when it binds to HslU in the presence of ATP[12]. The HslU has increased affinity for HslV in the presence of protein substrate.

In the HslvU complex, the Hs1U carboxy-terminal octapeptide EDLSRFIL (SEQ ID NO 3) (termed as HslU C-tail) is intercalated into a cleft between adjacent Hslv subunits with a network of interactions. Several polar amino acid residues (Lys28 and Arg35) and hydrophobic residues (Phe54) of Hslv form electrostatic and hydrophobic interactions respectively with side chain and main chain atoms of C-tail residues (FIG. 1). This C-tail insertion is accompanied by a conformational change in the active site of Hslv which resulted in allosteric activation of proteolytic activity of HslV. Therefore, the HslU C-tail acts as allosteric activator of Hslv protease. The observation that Hslv can be activated by synthetic peptides comprising the HslU carboxy-terminal sequence (C-tail) confirmed the role of this peptide in allosteric activation as well as in HslvU complex formation.

Orthologues of prokaryotic HslV and HslU in parasitic protozoa i.e. *Trypnosoma brucei* (causative agent of sleeping sickness), *Plasmodium falciparum* (causative agent of malaria) and *Leishmania* species (causative agent of leishmaniasis) are novel drug target candidates. The genes homologous to protozoal HslVU are not present in human genome. Therefore, intracellular protein degradation by activation of HslVU system has been considered as a innovative strategy for development of new antiparasitic agents. No other molecule is known to be capable of activating HslV in the absence of its natural activator, HslU. We have identified quanazoline and chromone derivatives as HslV activators in the presence of HslU.

BRIEF SUMMARY OF THE INVENTION

The HslVU is the proteasome-related two component system composed of HslV peptidase and HslU chaperone. It is involved in the degradation of an array of intracellular proteins. The presence of HslVU homologs in pathogenic microbes and its absence in human makes it an antimicrobial drug target. The functional HslVU complex forms when HslV dodecamer is flanked at both ends by HslU hexamers.

In the HslVU complex, eight residues at the carboxy termini of HslU subunits intercalate into a clefts between two adjacent HslV subunits causing a conformational change in the active site of HslV which in turn results in the allosteric activation of HslV peptidase. Here, small molecules capable of activating HslV peptidase in the absence of its natural activator HslU ATPase. For this purpose, virtual screening of an in-house library of synthetic and natural compounds was performed to find out ligands mimicking the interaction of HslU carboxy terminus with HslV dodecamer. The quinazoline and chromone derivatives were suggested by ligand docking to bind at the HslU carboxy termini intercalation pockets in the HslV dodecamer. The results showed for the first time that small, extracellular non-peptidic molecules can allosterically activate the peptide hydrolytic activity of HslV which in turn would initiate intracellular proteolysis.

BRIEF DESCRIPTION OF THE DRAWING

FIG. 1 depicts the HslVU protease-chaperone structure. (a) Dodecameric structure of HslV is stacked by tow hexameric rings of HslU. The carboxy-terminal actapeptide of HslU is intercalated into a cleft between adjacent HslV subunits. (b) Diagrammatic representation of HslV dodecamer. (c) Surface representation of HslV dimer interface complexed with the HslU-C-tail in ball-stick representation.

FIG. 2 depicts a sequence alignment of Hslv from *E. coli* (SEQ ID NO 1) and *H. influenza* (SEQ ID NO 2) used for homology model building. Helices (H1-H4) and strands (S 1-S9) are shaded in different colors. Conserved residues are mentioned with asterick.

FIG. 3 depicts the activation of *E. coli* HslV peptidase by *E.coli* HslU chaperone/ATPase[20].

FIG. 4 depicts *E. coli* HslV peptidase activation plots as a function of different concentrations of HslU C-tail octapeptide and compounds 1 and 2. $ED_{50}$ values were calculated from the plots of Vi/Vo versus compound concentration in which Vi and Vo were the velocities in the presence and absence of the compound[20].

FIG. 5A depicts a schematic 2-D representations of predicted binding modes of tested compound 3-[(E)-[(2-hydroxynaphthalen-1-yl)methylidene]amino]-2-(4-nitrophenyl)-3, 4-dihydroquinazolin-4-one, in the C-tail binding cleft of HslV. Thin lines are indicating intermolecular cation-pi and pi-pi interactions.

FIG. 5B depicts a schematic 2-D representations of predicted binding modes of tested compound N"-[(1E)-(4-oxo-4H-chromen-2-yl)methylidene]benzohydrazide, in the C-tail binding cleft of HslV. Thin lines are indicating intermolecular cation-pi and pi-pi interactions.

DETAILED DESCRIPTION OF THE INVENTION

We identified of two synthetic non-peptidic HslV peptidase activators. For this purpose, virtual screening was carried out by FlexX ligand docking software (version 2.0) using an in-house library of >1000 synthetic compounds and homology model of E. coli HslV. The 3D homology model was constructed by Modeller[19] using the crystal structure of H. infleuinzae7 (PDB id: 1G3I) and pairwise alignment of HslV from E. coli and H. infleunzae (FIG. 2). Due to significant sequence conservation between bacterial and protozoal HslVU, the E. coli HslV was used as a model system during this study. The in-house library compounds correspond to more than thirty different chemical scaffolds that have been synthesized in our laboratory. 3D models of compounds in SYBYL mol2 format were utilized for docking in to the C-tail binding cleft at the interface of two HslV subunits (FIG. 1). FlexX ligand docking was carried out allowing full flexibility for the ligands, while keeping the proteins fixed. After each ligand docking run, 10 top ranking docking solutions of each compound were saved and considered for detailed analysis (Table I).

Table I: Structures and $ED_{50}$ values of HslV protease activating compounds.

TABLE I

Structures and $ED_{50}$ values of HslV protease activating compounds.

| Compound No. | Structure | E. coli HslV activation (ED50 in µM) |
|---|---|---|
| 1 | [structure: quinazoline derivative with NO2 and naphthol groups] | 0.9 ± 0.25 |
| 2 | [structure: chromone derivative] | 1.3 ± 0.4 |

Figure 3:
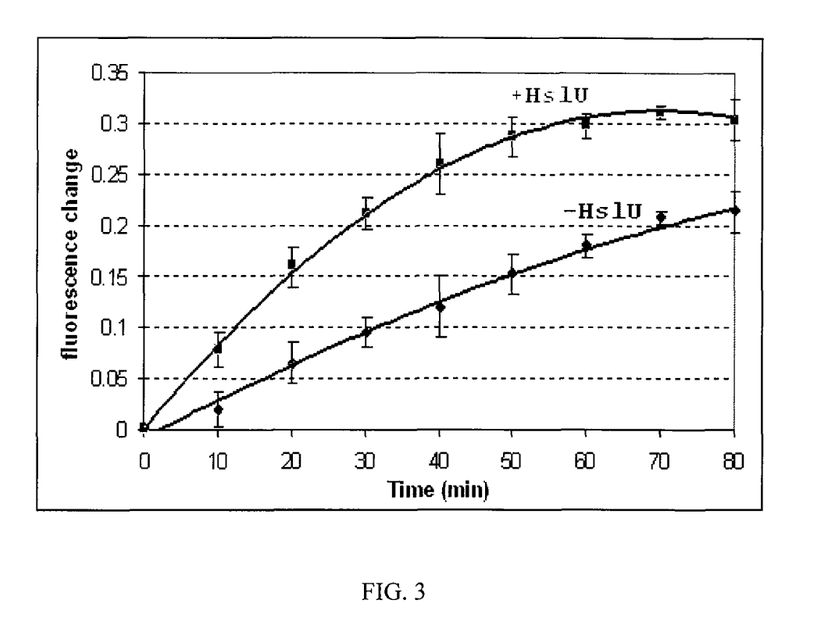

Virtual screening predicted derivatives of quinazoline (compound 1) and chromone (compound 2) and as potential HslV activators by docking them into the C-tail intercalation site with highest scores. These compounds mimic the binding of HslU C-tail at the interface of two adjacent HslV protomers. These compounds were tested for HslV activation in the absence of its natural activator HslU or HslU C-tail. Synthetic procedures of these compounds have been reported elsewhere. The HslV activation assays were carried out with recombinant E. coli HslV and HslU. Recombinant HslV and HslU were expressed in E. coli BL21 (DE3) cells containing pET20B+ vector. Purification of both proteins was carried out using Ni-chelating and ion-exchange chromatography as reported elsewhere[4]. Activation of HslV by HslU was monitored where HslV alone was found to be capable of catalyzing slow hydrolysis of the fluorogenic peptide substrate (Z-Gly-Gly-Leu-AMC) due to its basal peptidase activity for smaller substrates. In the presence of HslU and HslU C-tail, the rate of peptide hydrolysis was increased showing the already reported allosteric activation of HslV by HslU (FIG. 3).

Figure 4:
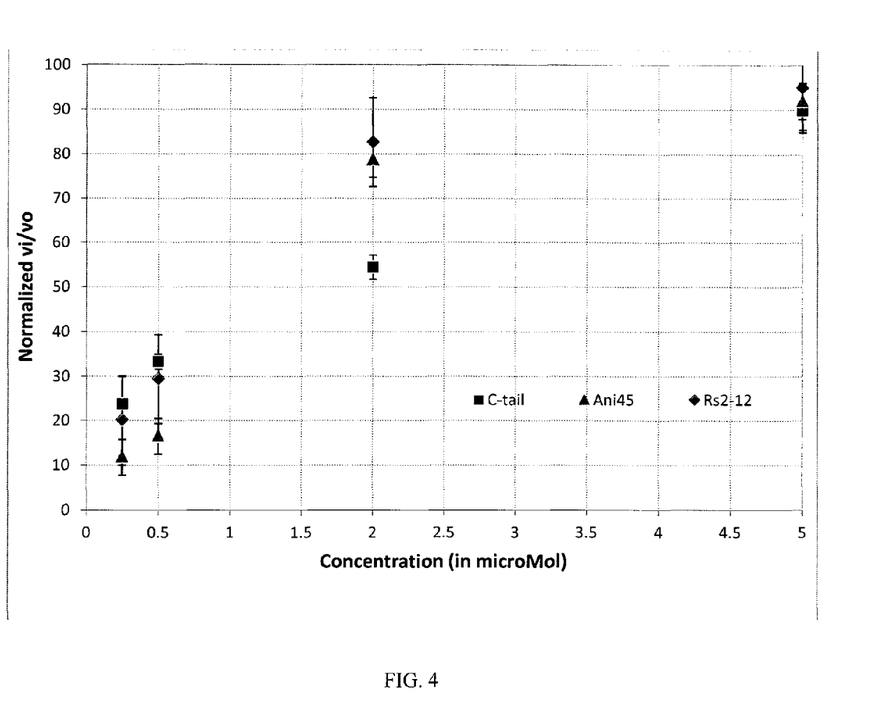

A concentration dependent activation of HslV was observed by the hit compounds in the absence of HslU or C-tail. Plots of HslV peptidase activity as a function of compound concentrations were constructed (FIG. 4). The effective dose of each compound at which HslV showed half maximal reaction velocity (i.e. $ED_{50}$) was calculated. The calculated $ED_{50}$ values of compounds were found in the range of 0.9-1.3 µM (Table 1). Under the same experimental conditions, $ED_{50}$ of HslU C-tail was determined as 2.6 µM.

Three dimensional structural analyses of the predicted binding modes of these compounds provided the basis of HslV activation from the structural point of view. The top five docking solutions of these compounds were modeled into the HslU C-tail binding site of HslV to investigate the interactions with protein residues. Analysis of docking solutions predicted the positioning of these compounds near the bottom of the HslV≡HslV protomer interface in the HslV dodecamer. HslV protomer interactions play a key role in HslV dodecamer stability and activity. It is well documented that protein-protein interactions depend on a few residues, or hot spots, at the binding interface. Dodecameric structure of HslV has "intra-ring" and "inter-ring" protomer interfaces. The HslU C-tail interaction site is at the "intra-ring" between two adjacent HslV protomers (or subunits; designated here as protomer A and B) (FIG. 1). The key interactions at A≡B interface are between (a) protomer A residues 50-58 and protomer B residues Arg83 and Asp111 and (b) protomer-A Lys28 and protomer-B Gln114. Previous structural analysis of HslVU characterized Lys28, Arg83 and Asp111 as hot spots at this HslU-intercalating interface[11].

Figure 5A:
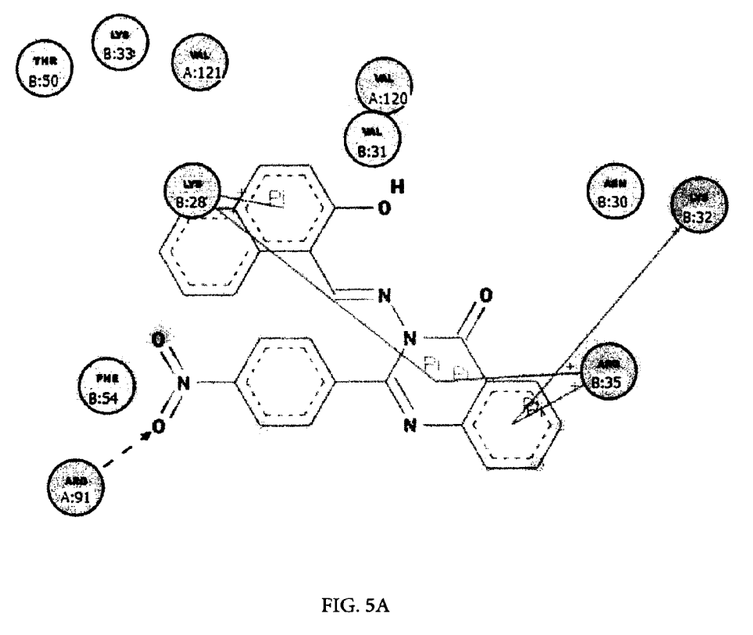
Figure 5B:
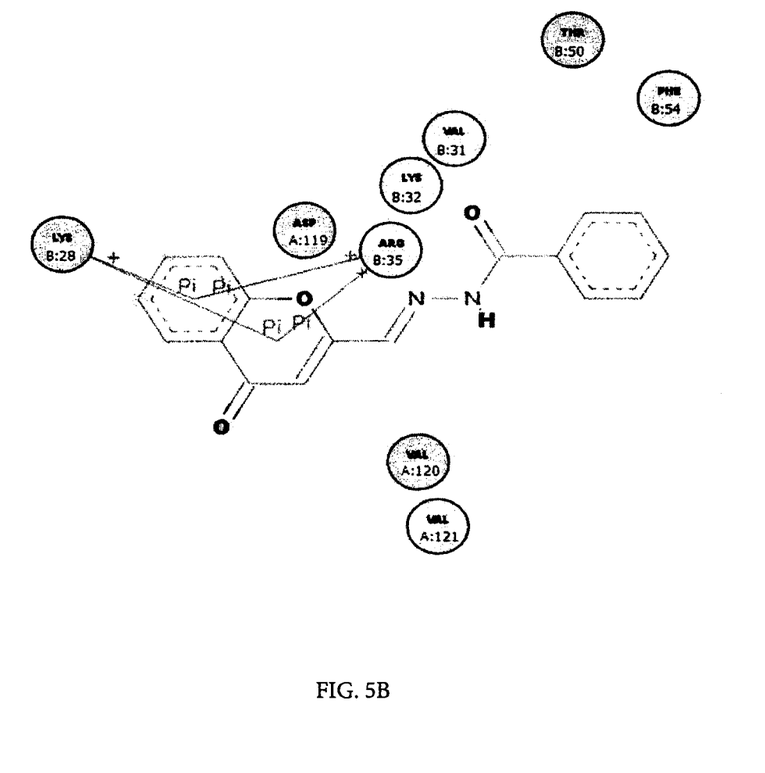

2D maps of ligand-protein interactions were generated by options available in Discovery Studio 3.1 (www.accelrys.com). These 2D maps elaborated a number of intermolecular interactions predicted in ligand-HslV complex (FIGS. 5A and 5B). Elaborated aromatic system in compound 1 was predicted to form cation-pi interactions with Lys28, Arg35 and Lys32 residues. The Phe54, Val31 and Val120 formed pi-pi interactions and hydrophobic contacts with compound 1 (FIG. 5A). Nitro group in compound 1 formed electrostatic interactions with Arg91. The two aromatic rings in compound 2 formed cation pi interactions with Lys28 and Arg35. Similarly, Phe54, Val31 and Val121 formed pi-pi interactions and hydrophobic interactions respectively (FIG. 5B). This analysis showed that HslV activating small molecules formed energetically favorable interactions with several residues in particular hot spots residues Lys28 and Val120 at the HslV interface[11]. Our data indicate that hot spots and cluster forming residues at the HslV interface play important role in binding of activating molecules.

Ligand docking studies provided valuable information related to structural basis of binding of these compounds at the C-tail binding pocket in the HslV dodecamer. The HslV activation assays showed that synthetic, non-peptidic small molecules can bind and allosterically activate the peptide hydrolytic activity of HslV with $ED_{50}$ values lower than HslU C-tail. For this reason, such compounds would initiate intracellular proteolysis in bacterial and protozoal cells and would provide a novel mechanism of antimicrobial action.

What is claimed is:

1. A method of activating a HsIV peptidase enzyme in a pathogenic organism by contacting the organism with a sufficient quantity of 3-[(E)-[(2-hydroxynaphthalen-1-yl)methylidene]amino]-2-(4-nitrophenyl)-3,4-dihydroquinazolin-4-one.

* * * * *

SEQUENCE LISTING

<160> NUMBER OF SEQ ID NOS: 3

<210> SEQ ID NO 1
<211> LENGTH: 173
<212> TYPE: PRT
<213> ORGANISM: Escherichia coli

<400> SEQUENCE: 1

Thr Thr Ile Val Ser Val Arg Arg Asn Gly His Val Val Ile Ala Gly
1               5                   10                  15

Asp Gly Gln Ala Thr Leu Gly Asn Thr Val Met Lys Gly Asn Val Lys
            20                  25                  30

Lys Val Arg Arg Leu Tyr Asn Asp Lys Val Ile Ala Gly Phe Ala Gly
        35                  40                  45

Gly Thr Ala Asp Ala Phe Thr Leu Phe Glu Leu Phe Glu Arg Lys Leu
    50                  55                  60

Glu Met His Gln Gly His Leu Val Lys Ala Ala Val Glu Leu Ala Lys
65                  70                  75                  80

Asp Trp Arg Thr Asp Arg Met Leu Arg Lys Leu Glu Ala Leu Leu Ala
                85                  90                  95

Val Ala Asp Glu Thr Ala Ser Leu Ile Ile Thr Gly Asn Gly Asp Val
            100                 105                 110

Val Gln Pro Glu Asn Asp Ile Ala Ile Gly Ser Gly Gly Pro Tyr Ala
        115                 120                 125

Gln Ala Ala Arg Ala Leu Leu Glu Asn Thr Glu Leu Ser Ala Arg
    130                 135                 140

Glu Ile Ala Glu Lys Ala Leu Asp Ile Ala Gly Asp Ile Cys Ile Tyr
145                 150                 155                 160

Thr Asn His Phe His Thr Ile Glu Glu Leu Ser Tyr Lys
                165                 170

<210> SEQ ID NO 2
<211> LENGTH: 173
<212> TYPE: PRT
<213> ORGANISM: Haemophilus influenzae

<400> SEQUENCE: 2

Thr Thr Ile Val Ser Val Arg Arg Asn Gly Gln Val Val Gly Gly
1               5                   10                  15

Asp Gly Gln Val Ser Leu Gly Asn Thr Val Met Lys Gly Asn Ala Arg
            20                  25                  30

Lys Val Arg Arg Leu Tyr Asn Gly Lys Val Leu Ala Gly Phe Ala Gly
        35                  40                  45

Gly Thr Ala Asp Ala Phe Thr Leu Phe Glu Leu Phe Glu Arg Lys Leu
    50                  55                  60

Glu Met His Gln Gly His Leu Leu Lys Ser Ala Val Glu Leu Ala Lys
65                  70                  75                  80

Asp Trp Arg Thr Asp Arg Ala Leu Arg Lys Leu Glu Ala Met Leu Ile
                85                  90                  95

Val Ala Asp Glu Lys Glu Ser Leu Ile Ile Thr Gly Ile Gly Asp Val
            100                 105                 110

Val Gln Pro Glu Asp Gln Ile Leu Ala Ile Gly Ser Gly Gly Asn
        115                 120                 125

Tyr Ala Leu Ser Ala Ala Arg Ala Leu Val Glu Asn Thr Glu Leu Ser
    130                 135                 140

Ala His Glu Ile Val Glu Lys Ser Leu Arg Ile Ala Gly Asp Ile Cys

```
                145                 150                 155                 160
Val Phe Thr Asn Thr Asn Phe Thr Ile Glu Glu Leu Pro
                165                 170

<210> SEQ ID NO 3
<211> LENGTH: 8
<212> TYPE: PRT
<213> ORGANISM: Artificial Sequence
<220> FEATURE:
<223> OTHER INFORMATION: HsIVUC tail

<400> SEQUENCE: 3

Glu Asp Leu Ser Arg Phe Ile Leu
1               5
```